(12) United States Patent
Akiyama et al.

(10) Patent No.: US 11,426,136 B2
(45) Date of Patent: Aug. 30, 2022

(54) X-RAY DIAGNOSTIC SYSTEM AND MEDICAL IMAGE DIAGNOSTIC SYSTEM

(71) Applicant: TOSHIBA MEDICAL SYSTEMS CORPORATION, Otawara (JP)

(72) Inventors: Masaki Akiyama, Otawara (JP); Yoshimasa Kobayashi, Nasushiobara (JP); Jun Sakakibara, Otawara (JP); Keisuke Nakamura, Utsunomiya (JP); Satoru Ohishi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 509 days.

(21) Appl. No.: 15/388,117

(22) Filed: Dec. 22, 2016

(65) Prior Publication Data

US 2017/0181718 A1 Jun. 29, 2017

(30) Foreign Application Priority Data

Dec. 24, 2015 (JP) .............................. JP2015-252215
Dec. 21, 2016 (JP) .............................. JP2016-247691

(51) Int. Cl.
*A61B 6/00* (2006.01)
*A61B 6/12* (2006.01)
*A61B 6/04* (2006.01)

(52) U.S. Cl.
CPC ............ *A61B 6/4441* (2013.01); *A61B 6/465* (2013.01); *A61B 6/467* (2013.01); *A61B 6/487* (2013.01); *A61B 6/504* (2013.01); *A61B 6/587* (2013.01)

(58) Field of Classification Search
CPC ....... A61B 6/4441; A61B 6/587; A61B 6/467; A61B 6/465; A61B 6/504; A61B 6/487

(Continued)

(56) References Cited

U.S. PATENT DOCUMENTS

2003/0068011 A1\* 4/2003 Johnson ............... A61B 5/7475
378/115
2015/0124940 A1\* 5/2015 Kim ...................... A61B 6/547
378/189
2015/0182297 A1\* 7/2015 Sandhu ................... A61B 6/12
600/424

FOREIGN PATENT DOCUMENTS

EP      0 829 228 A1    3/1998
JP      10-63812        3/1998
(Continued)

OTHER PUBLICATIONS

Japanese Office Action dated Jan. 5, 2021, issued in Japanese Patent Application No. 2016-247691.

*Primary Examiner* — Michael W Kahelin
*Assistant Examiner* — Pamela M. Bays
(74) *Attorney, Agent, or Firm* — Oblon, McClelland, Maier & Neustadt, L.L.P.

(57) ABSTRACT

According to one embodiment, an X-ray diagnostic system is used with an operation apparatus for operating, from a position separated from an object, a device inserted inside the object, and includes an imaging apparatus, an designation receiving circuit, a first display, and a second display. The imaging apparatus performs X-ray imaging of the object. The designation receiving circuit receives designation of a position on medical data from a first user who operates the device. The first display is disposed at a position visible from the first user, and displays a first image according to the designation of the position. The second display is disposed at a position visible from a second user who performs positioning of the imaging apparatus, and displays a second image different from the first image according to the designation of the position.

23 Claims, 8 Drawing Sheets

(58) Field of Classification Search
USPC .......................................................... 600/424
See application file for complete search history.

(56) References Cited

FOREIGN PATENT DOCUMENTS

| | | |
|---|---|---|
| JP | 10-94529 | 4/1998 |
| JP | 2003-265454 A | 9/2003 |
| JP | 2007-190199 | 8/2007 |
| JP | 2010-155098 | 7/2010 |
| JP | 2013-047940 A | 3/2013 |
| JP | 2015-37572 | 2/2015 |
| WO | WO 2004/062497 A1 | 7/2004 |
| WO | WO 2009/137410 A1 | 11/2009 |

* cited by examiner

X-RAY DIAGNOSTIC SYSTEM AND MEDICAL IMAGE DIAGNOSTIC SYSTEM

CROSS-REFERENCE TO RELATED APPLICATIONS

This application claims the benefit of priority of Japanese Patent Application No. 2015-252215, filed Dec. 24, 2015, and Japanese Patent Application No. 2016-247691, filed Dec. 21, 2016, the entire contents of all of which are incorporated herein by reference.

FIELD

Embodiments described herein relate generally to an X-ray diagnostic system and a medical image diagnostic system.

BACKGROUND

When performing catheter treatment, a user may perform manipulation by causing an X-ray fluoroscopic image and an X-ray radiographic image (hereafter, referred to as an X-ray image), which are based on X-ray imaging by an X-ray diagnostic apparatus, to be displayed during manipulation, and confirming the position of a device such as a catheter and a guide wire which are depicted on an X-ray image.

As a technology to support this type of manipulation, there is for example a remote catheter system. According to the remote catheter system, since the operator can remotely control the device, it is possible to reduce X-ray exposure of the operator.

When an operator remotely operates a devise using a remote catheter system, positioning of an imaging system of an X-ray diagnostic apparatus is performed by a person except the operator (hereinafter, referred to as a medical engineer) in some cases. In order to provide an operator with desired X-ray images in such cases, it is required for a medical engineer to adjust an X-ray imaging region and an X-ray imaging direction (hereinafter, referred to as an imaging region and an imaging direction, respectively) by remotely operating an imaging system and a bed of an X-ray diagnostic apparatus.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray diagnostic system and a medical image diagnostic system according to embodiments of the present invention with reference to the drawings.

According to one embodiment, an X-ray diagnostic system is used with an operation apparatus for operating, from a position separated from an object, a device inserted inside the object, and includes an imaging apparatus, a designation receiving circuit, a first display, and a second display. The imaging apparatus performs X-ray imaging of the object. The designation receiving circuit receives designation of a position on medical data from a first user who operates the device. The first display is disposed at a position visible from the first user, and displays a first image according to the designation of the position. The second display is disposed at a position visible from a second user who performs positioning of the imaging apparatus, and displays a second image different from the first image according to the designation of the position.

Figure 1:
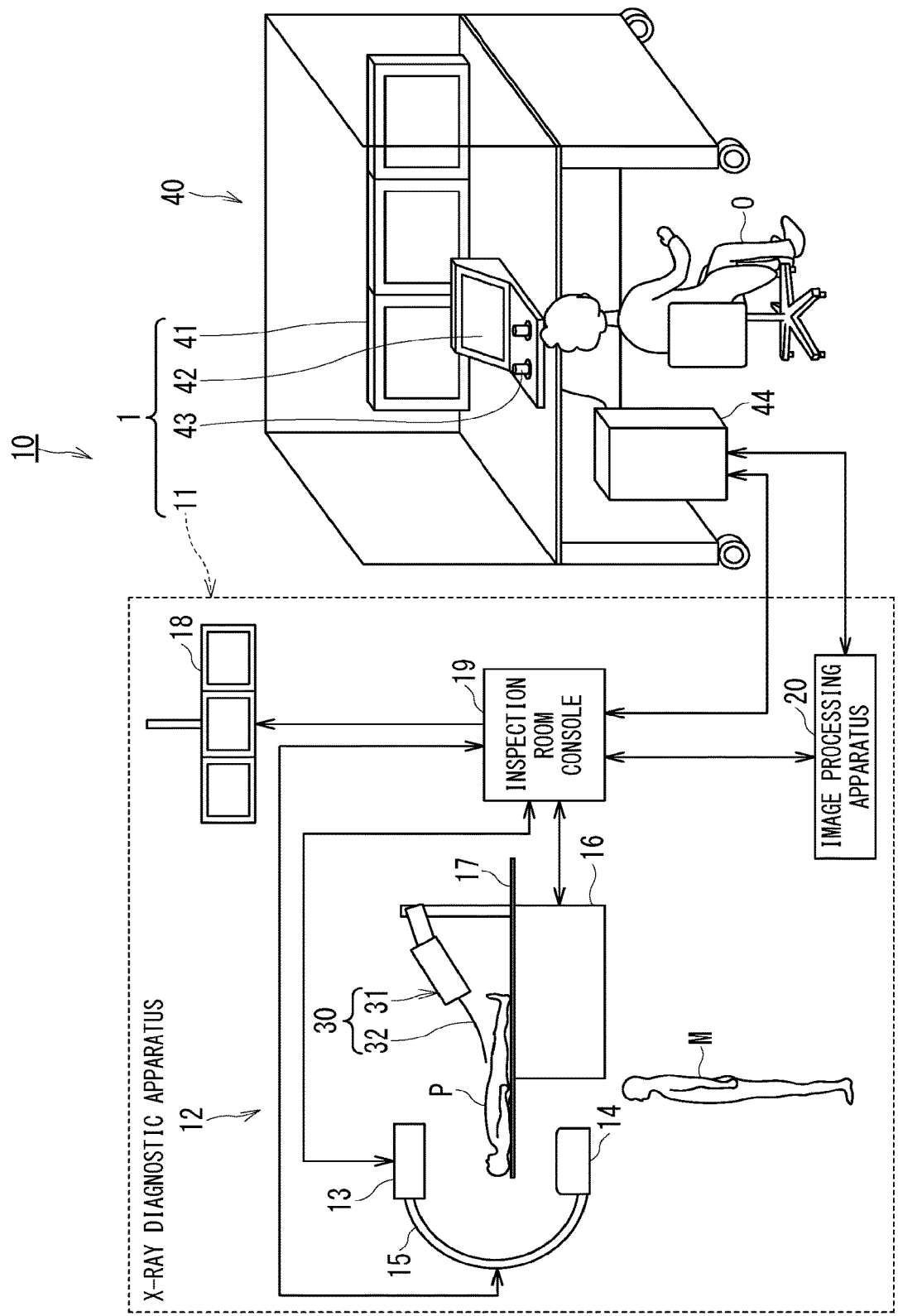
FIG. 1 is a block diagram illustrating a medical image diagnostic system including an X-ray diagnostic system according to one embodiment of the present invention.

FIG. 1 is a block diagram illustrating a medical image diagnostic system 10 including an X-ray diagnostic system 1 according to one embodiment of the present invention.

The X-ray diagnostic apparatus 11 is configured as, for example, an angiography apparatus, and includes an imaging apparatus 12 and an image processing apparatus 20 as shown in FIG. 1. The imaging apparatus 12 of the X-ray diagnostic apparatus 11 is generally installed on an inspection room, and is configured to generate X-ray projection data of an object P. The image processing apparatus 20 is, e.g., installed on an operators room adjacent to the inspection room, and is configured to generate X-ray images based on X-ray projection data and cause a display to display the generated X-ray images. Note that the image processing apparatus 20 may be installed on the inspection room where the imaging apparatus 12 is installed. In the present embodiment, the image processing apparatus 20 operates not according to operations performed by an operator O as a first user but according to operations performed by a medical engineer M in the inspection room as a second user.

The medical image diagnostic system 10 includes a remote catheter 30 and a remote console 40 in addition to the X-ray diagnostic apparatus 11. The remote catheter 30 and the remote console 40 constitute a so-called remote catheter system. In the present embodiment, the operator O who remotely controls a device 32 inserted inside the object P by operating the remote console 40 is a user except the medical engineer M.

The X-ray diagnostic system 1 includes a display disposed at a position visible from the operator O and a designation receiving circuit configured to receive designation for operations with respect to a remote catheter 30, in addition to the X-ray diagnostic apparatus 11. The device 32 of the remote catheter 30 which is inserted inside the object P to be imaged by the X-ray diagnostic apparatus 11 of the X-ray diagnostic system 1 is operated from a position remote from the object P. The designation receiving circuit is realized as, e.g., a remote input circuit 43 of the remote console 40. Additionally, the display disposed at a position visible from the operator O is realized as, e.g., a display 71 of the image processing apparatus 20 and/or a display of a display input circuit 41 or 42 of the remote console 40.

The imaging apparatus 12 of the X-ray diagnostic apparatus 11 includes an X-ray detector 13, an X-ray source 14, a C-arm 15, a bed 16, a tabletop 17 of the bed 16, a display 18, and an inspection room console 19.

The X-ray detector 13 is provided at one end of the C-arm 15 so as to be opposed to the X-ray source 14 with the object P supported by the tabletop (for example, a catheter table, etc.) 17 of the bed 16 being interposed therebetween. The X-ray detector 13, which is made up of a flat plane detector (FPD), detects X-rays which are radiated to the X-ray detector 13 passing through the object P, and outputs projection data of X-ray based on the detected X-rays. This projection data is provided to the image processing apparatus 20 via the inspection room console 19. Note that the X-ray detector 13 may include an image intensifier, a TV camera, or the like.

The X-ray source 14 is provided on the other end of the C-arm 15, and includes an X-ray bulb and an X-ray aperture. The X-ray aperture is an X-ray irradiation field aperture configured of, e.g., plural lead blades. The X-ray aperture adjusts an X-ray irradiation range radiated from the X-ray bulb under the control of the inspection room console 19.

The C-arm 15 integrally holds the X-ray detector 13 and the X-ray source 14. When the C-arm 15 is controlled by the inspection room console 19 and driven, the X-ray detector 13 and the X-ray source 14 are integrally moved around the object P. The X-ray detector 13, the X-ray source 14, and the C-arm 15 constitute an imaging system for performing X-ray imaging of the object P.

The X-ray imaging by the imaging system includes so-called fluoroscopy and radiography. Fluoroscopy is X-ray imaging to acquire an image by X-ray irradiation with a weaker X-ray irradiation intensity compared with radiography. For that reason, although the resolution of a fluoroscopic image acquired by fluoroscopy is lower than that of a radiographic image acquired by radiography, X-ray dose to which the object P is exposed in fluoroscopy is lower than in radiography. Therefore, fluoroscopy is suitable when it is desirable to confirm an X-ray image of the object P in an animating manner in real time. On the other hand, although X-ray dose to which the object P is exposed is higher, the image quality is clearer in radiography than in fluoroscopy. In the following description, fluoroscopy and radiography are conveniently referred to as X-ray imaging, and an X-ray fluoroscopic image and an X-ray radiographic image based on X-ray imaging are conveniently referred to as an X-ray image.

Moreover, when the X-ray diagnostic apparatus 11 is used as an angiography apparatus, the X-ray diagnostic apparatus 11 may be of a biplane type having two lines of imaging system which is made up of the X-ray detector 13, the X-ray source 14, and the C-arm 15 and captures an X-ray image of the object P. In the case of biplane type, the X-ray diagnostic apparatus 11 can acquire a biplane image (F (frontal) side image and L (lateral) side image) by causing an X-ray beam to be radiated separately from each of two directions of the F side having a floor mounted C-arm and the L side having a ceiling travelling Q-arm.

The bed 16 is installed on a floor surface and equipped with the tabletop 17 for placing the object P. The bed 16 moves the tabletop 17 in a horizontal direction and in a vertical direction and rotates the tabletop 17 under the control of the inspection room console 19.

The display 18 has one or plural display regions, and displays various types of information such as a provisional image for positioning (hereinafter, referred to as a positioning provisional images) and a fluoroscopic image being updated on a real-time basis under the control of the inspection room console 19. The display 18 is configured of a general display output device such as a liquid-crystal display, an OLED (Organic Light Emitting Diode) display.

The inspection room console 19 is controlled by the image processing apparatus 20, and controls the X-ray detector 13 so as to perform X-ray imaging of the object P and generate projection data. The inspection room console 19 outputs the projection data to the image processing apparatus 20. The inspection room console 19 is controlled by the image processing apparatus 20 and generates, e.g., projection data before and after administration of a contrast medium so as to output the generated projection data to the image processing apparatus 20. For instance, the inspection room console 19 may be a satellite console configured to be capable of freely moving on the floor of the inspection room.

When the X-ray diagnostic apparatus 11 is configured so as to be capable of rotation DSA (Digital Subtraction Angiography) imaging, the inspection room console 19 performs the rotation DSA imaging so as to generate projection data before and after administration of a contrast medium and output the generated projection data to the image processing apparatus 20, under the control of the image processing apparatus 20. In the case of the rotation DSA imaging, image data before administration of the contrast medium (i.e., mask image data) and image data after the administration of the contrast medium (i.e., contrast image data) are generated with respect to the same portion of the same object P. When the rotation DSA imaging is practicable, the X-ray diagnostic apparatus 11 can also acquire a three-dimensional blood vessel image on the basis of the mask image data and the contrast image data acquired by the rotation DSA imaging.

The inspection room console 19 includes at least a processor and memory circuitry. The inspection room console 19 is controlled by the image processing apparatus 20 according to programs stored in this memory circuitry so as to perform X-ray imaging such as fluoroscopy of the object P by controlling the imaging system and output the projection data.

Although FIG. 1 illustrates a case where the inspection room console 19 and the image processing apparatus 20 are connected with each other by wire, the inspection room console 19 and the image processing apparatus 20 may be connected with each other so as to be capable of data transmission/reception via a network.

Additionally, the X-ray diagnostic apparatus 11 may include a non-illustrated injector. In this case, the injector injects a contrast medium through the device 32 of the remote catheter 30 having been inserted into an affected area of the object P under the control of the inspection room console 19. The timings of injection and stopping of the contrast medium, and the density and injection rate of the contrast medium are automatically controlled by the inspection room console 19. Moreover, the present embodiment is not limited to causing the injector to operate under the control of the inspection room console 19. For instance, an instruction by the medical engineer M may be received via an input unit installed on the injector such that the contrast medium is injected at a concentration, at a speed, and at a timing according to this instruction. Similarly, an instruction by the operator O may be received via the remote console 40 such that the contrast medium is injected at a concentration, at a speed, and at timing according to this instruction.

The remote catheter 30 of the remote catheter system as an example of a remote control system includes a robot arm 31 and the device 32, and is configured to insert the device 32 into a predetermined portion (e.g., an affected area) of the object P under the control of the remote console 40. Additionally, the remote catheter 30 may be configured to be capable of remote controlling plural devices 32.

The X-ray diagnostic apparatus 11 of the present embodiment assists the medical engineer M in adjusting an imaging region and an imaging direction such that images desired by the operator O of the device 32 are acquired, and this assistance method will be briefly described.

As to operations of the imaging apparatus 12, various operations such as movement of the imaging system, movement of the bed and its tabletop 17, X-ray imaging performed by the imaging system, and administration of a contrast medium controlled by the non-illustrate injector are included. However, it is difficult for the operator O of the device 32 to confirm the current conditions around the imaging apparatus 12 in detail. This is because the operator O is at a position remote from the inspection room or sight of the operator O is blocked by a protection board of the remote console 40 even if the remote console 40 is installed in the inspection room. Thus, if the operator O remotely controls the imaging apparatus 12, it is difficult for the operator O to accurately recognize positional relationship between operation targets of the remote control and obstacles in the vicinity of those operation targets (e.g., mechanical component of the imaging apparatus 12 and a person such as the object P). For this reason, it is desirable that the imaging apparatus 12 acts not according to operations performed by the operator O but according to operations performed by the medical engineer M in the inspection room.

Thus, in the present embodiment, the imaging apparatus 12 acts not according to operations performed by the operator O but according to operations performed by the medical engineer M in the inspection room. Not the medical engineer M but the operator O actually performs medical treatment while confirming X-ray images. Hence, in order to acquire X-ray images desired by the operator O of the device 32, it is required that the medical engineer M adjusts positional relationship between the imaging system and the bed 16 of the imaging apparatus 12.

For the above reason, the X-ray diagnostic apparatus 11 of the present embodiment acquires information on an imaging region and an imaging direction of desirable X-ray images from the operator O of the device 32 via the remote input circuit 43 of the remote console 40 or an input circuit 72 of the image processing apparatus 20 in the operators room. The desirable X-ray images are the images that operator O desires to observe during the medical treatment. Hereinafter, an imaging region and an imaging direction of desired X-ray images in the above description are referred to as a desired region and a desired direction, respectively. Then, the X-ray diagnostic apparatus 11 provides the medical engineer M with a provisional image for positioning (hereinafter, referred to as a positioning provisional image) which is appropriate for assistance in positioning of the imaging apparatus 12 performed by the medical engineer M, according to the desired region and the desired direction. At the same time, the X-ray diagnostic system 11 provides the operator O with a provisional image for medical treatment (hereinafter, referred to as an operative provisional image) which is appropriate for assistance in medical treatment performed by the operator O of the device 32, according to the desired region and the desired direction.

The remote console 40 includes display input circuits 41 and 42, a remote input circuit 43 for remotely controlling the device 32 of the remote catheter 30, and a controller 44.

Each of the display input circuits 41 and 42 includes a display and a touch sensor provided in the vicinity of this display. The display is configured of a general display output device such as a liquid-crystal display and an OLED display. The touch sensor outputs information on an instruction position on the touch sensor pointed by a user to processing circuitry of the controller 44. When the touch sensor is configured of, e.g., an electrostatic capacity panel of a projection type, the touch sensor has electrode rows arranged vertically and horizontally. In this case, the touch sensor can acquire a contact position based on output change of the electrode row according to change in electrostatic capacity in the vicinity of the contact position of a contact object.

The display of the display input circuit 41 is controlled by the processing circuitry of the controller 44 and displays, e.g., an image similar to that on the display 18. When the operator O of the device 32 inputs information for setting the desired region and the desired direction into the controller 44 via the remote input circuit 43, the display of the display input circuit 41 displays an operative provisional image.

The display of the display input circuit 42 is controlled by the processing circuitry of the controller 44 and displays, e.g., information on a control target device of the remote input circuit 43. Additionally, the display of the display input circuit 42 may display an operative provisional image when the operator O of the device 32 inputs information for setting the desired region and the desired direction into the controller 44 via the remote input circuit 43.

The remote input circuit 43 includes a hand switch for instructing an X-ray exposure timing and a general pointing device such as a track ball, a track ball mouse, a keyboard, a touch panel, a ten-key, a voice input circuit, and eye-gaze input circuit. The remote input circuit 43 outputs a signal for remotely controlling the device 32 to the remote catheter 30 via the controller 44 by wire or wirelessly, when being operated by the operator O.

Moreover, the remote input circuit 43 provides the controller 44 with information for setting the desired region and the desired direction of a desirable X-ray image which the operator O of the device 32 uses during manipulation of medical treatment, when being operated by the operator O.

The controller 44 includes at least a processor and memory circuitry. The processing circuitry of the controller 44 is linked with the image processing apparatus 20 according to programs stored in this memory circuitry. For instance, the processing circuitry of the controller 44 outputs information on feed movement amount of the device 32 to the image processing apparatus 20. Additionally, the processing circuitry of the controller 44 provides the image processing apparatus 20 with information for setting the desired region and the desired direction inputted by the operator O via the remote input circuit 43.

Further, the remote console 40 may be provided with a speaker and a microphone which enable the operator O of the remote console 43 and the medical engineer M to communicate with each other in real time by phone, for instance.

Figure 2:
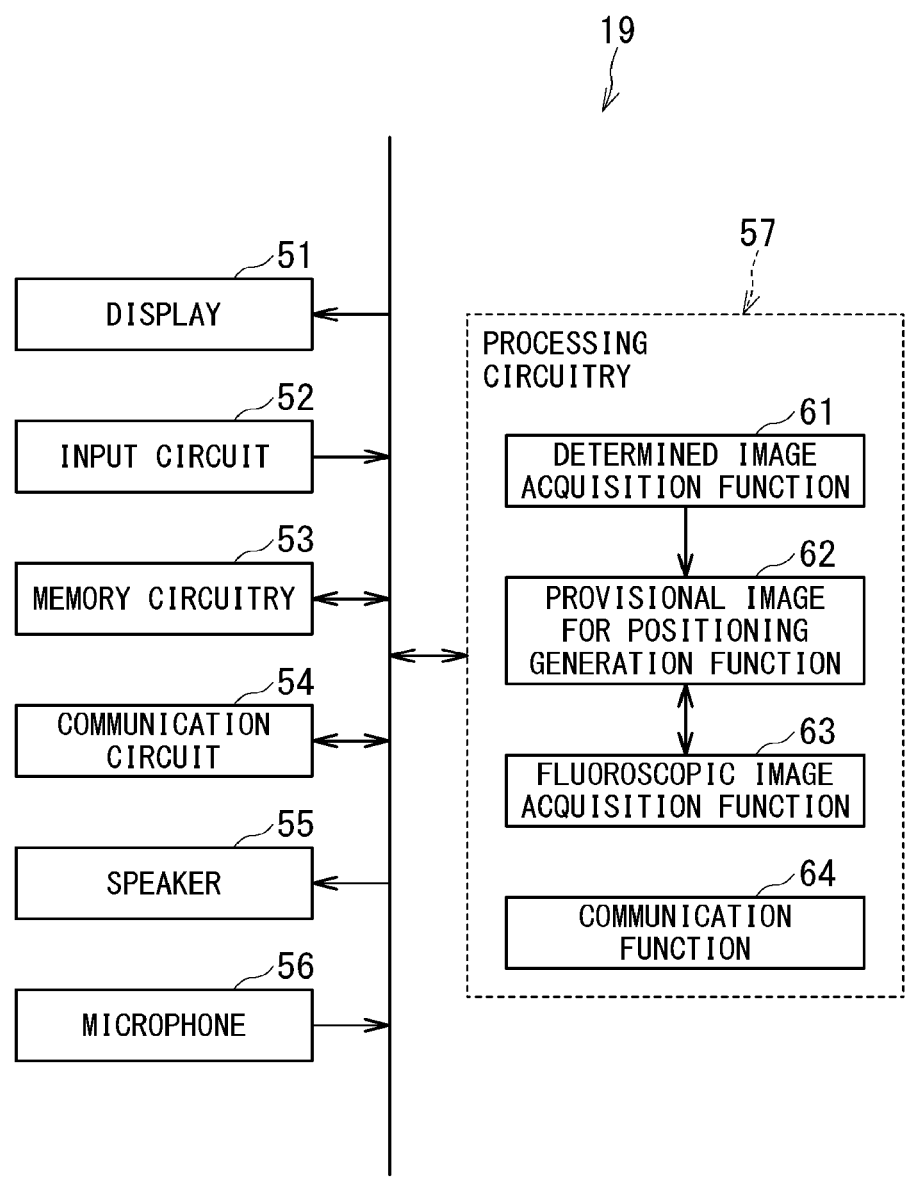
FIG. 2 is a block diagram illustrating configuration of an inspection room console.

FIG. 2 is a block diagram illustrating configuration of the inspection room console 19. The inspection room console 19 includes a display 51, an input circuit 52, memory circuitry 53, a communication circuit 54, a speaker 55, a microphone 56, and processing circuitry 57.

The display 51 is configured of a general display output device such as a liquid-crystal display and an OLED display, and displays various types of information such as a positioning provisional image and a fluoroscopic image to be updated on a real-time basis under the control of the processing circuitry 57. The input circuit 52 is configured of a general display device such as a keyboard, a touch panel, a track ball, a ten-key, a voice input circuit, a visual line input circuit, and outputs an input signal corresponding to an operation by the medical engineer M to the processing circuitry 57.

The memory circuitry 53 is equipped with configuration including a recording medium which can be read by the processor such as a magnetic or optical recording medium and/or a semiconductor memory. The memory circuitry 53 may be configured such that some or all of those programs and data in the recording medium are downloaded through an electronic network. The memory circuitry 53 previously or preliminarily stores three-dimensional medical image data of a human body diagram in imitation of a human body (hereinafter, referred to as 3D model data) as an example of medical data. Additionally, the memory circuitry 53 may previously store three-dimensional medical image data (hereinafter, referred to as volume data) of the object P which are acquired in advance. Hereinafter, 3D model data and volume data are collectively referred to as 3D data.

As to medical data, it is enough that medical data are data available for setting an imaging region and an imaging direction of an X-ray image which the operator O desires to refer to while performing manipulation with the use of the device 32. For instance, medical data may be two-dimensional medical image data, a list of anatomical data of, e.g., character strings indicating anatomical landmark, or combination of both. The operator O designates a position on medical data via the designation receiving circuit. The X-ray diagnostic system 1 causes the first display such as the display of the display input circuit 41 or 42 to display the first image according to the designated position, and causes the second display such as the display 18 to display the second image according to the designated position. Note that the second image is different from the first image.

Additionally, medical data may be prepared for each type of classification such as classification based on age of the object P including an adult and a child, classification based on gender, and classification based on body weight. In this case, the operator O may preferably select one set of medical data in consideration of the classification to which the object P belongs so as to instruct a position on the selected medical data.

In the present embodiment, a description will be given of a case where medical data are 3D data.

The communication circuit 54 implements various types of information communication protocols according to aspects of networks. The communication circuit 54 connects the inspection room console 19 with the controller 44 of the image processing apparatus 20 and the remote console 40 according to the various types of information communication protocols. In this connection, e.g., electric connection via electronic network can be applied. The electronic network means general information communication network using telecommunications technology and includes, e.g., a telephone communication network, an optical fiber communication network, a cable communication network, and a satellite communication network in addition to a wireless/wired LAN (Local Area Network) and the Internet network.

For instance, the processing circuitry 57 may acquire volume data of the object P from, e.g., an image server via a network and store the acquired data in the memory circuitry 53.

The speaker 55 and the microphone 56 are used, e.g., when the operator O of the image processing apparatus 20 in the operators room and the medical engineer M communicate with each other by phone or by video call in real time through voice information communication performed by the communication circuit 54. Additionally, the speaker 55 and the microphone 56 are used when the operator O of the remote console 40 in the operators room and the medical engineer M communicate with each other by phone or by video call in real time through voice information communication performed by the communication circuit 54.

The processing circuitry 57 is a processor configured to perform processing of assisting the medical engineer M in adjusting an imaging region and an imaging direction in cooperation with the processing circuitry 77 of the image processing apparatus 20 by reading out and executing programs stored in the memory circuitry 53 such that X-ray images desired by the operator O of the device 32 are acquired.

As shown in FIG. 2, the processing circuitry 57 implements a determined image acquisition function 61, a positioning provisional image generation function 62, a fluoroscopic image acquisition function 63, and a communication function 64. Those functions 61 to 64 are stored in the memory circuitry 53 in the form of programs.

Incidentally, the positioning provisional image generation function 62 may be implemented by the processing circuitry 77 of the image processing apparatus 20. In this case, the positioning provisional image generation function 62 may be omitted from the processing circuitry 57.

Figure 3:
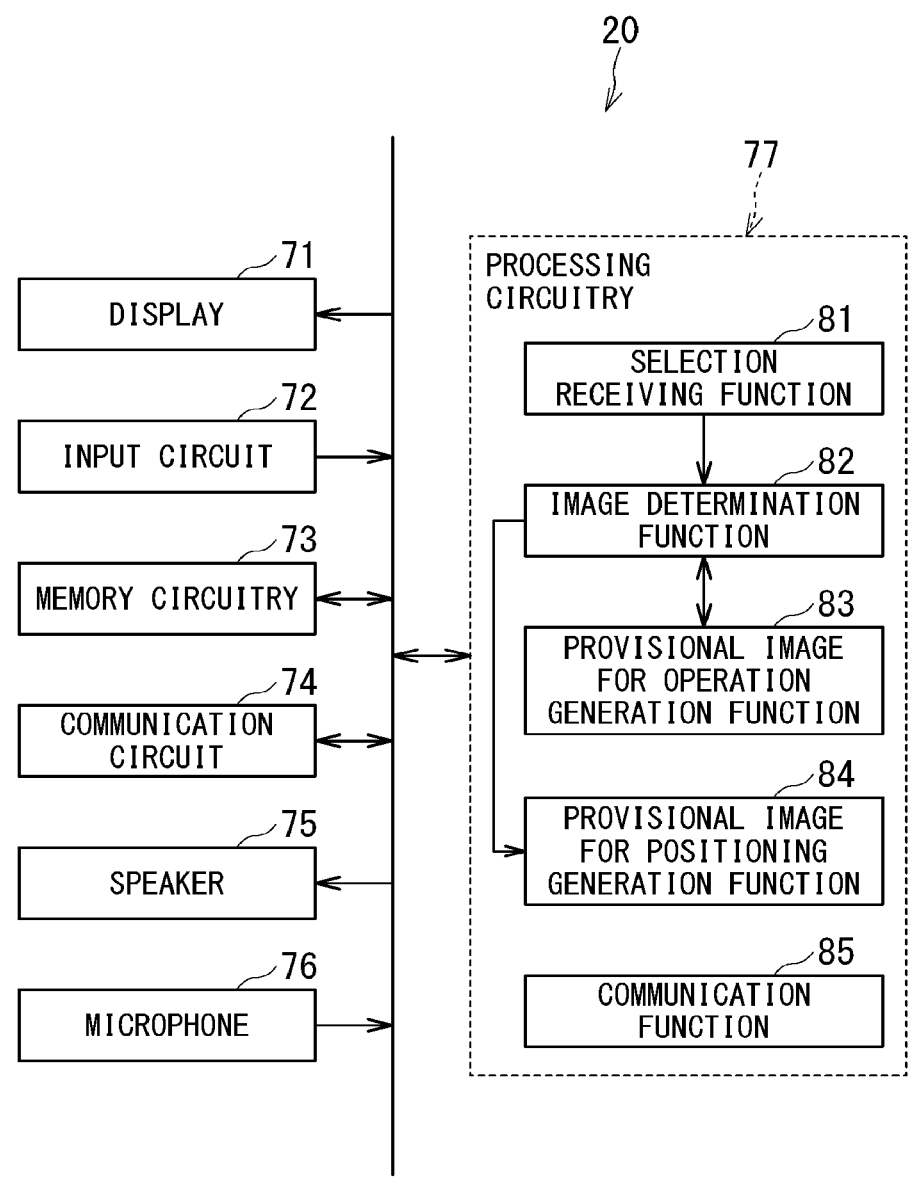
FIG. 3 is a block diagram illustrating configuration of an image processing apparatus.

FIG. 3 is a block diagram illustrating configuration of the image processing apparatus 20.

The image processing apparatus 20 includes a display 71, an input circuit 72, memory circuitry 73, a communication circuit 74, a speaker 75, a microphone 76, and processing circuitry 77.

The display 71 is configured of a general display output device such as a liquid-crystal display and an OLED display, and displays various type of information such as medical images under the control of the processing circuitry 77. Additionally, when the operator O of the device 32 provides the processing circuitry 77 with information for setting the desired region and the desired direction via the input circuit 72, the display 71 displays an operative provisional image.

The input circuit 72 is configured of, e.g., a general input device such as a keyboard, a touch panel, a track ball, a ten-key, a voice input circuit, and a visual line input circuit. The input circuit 72 outputs an input signal, which is in accordance with an operation performed by a user in the operators room including the medical engineer M and the operator O, to the processing circuitry 77. Additionally, when being operated by the operator O, the input circuit 72 provides the processing circuitry 77 with information for setting the desired region and the desired direction of an X-ray image which the operator O desires to refer to during manipulation with the use of the device 32.

The memory circuitry 73 is equipped with configuration including a recording medium which can be read by the processor such as a magnetic or optical recording medium and/or a semiconductor memory. The memory circuitry 73 may be configured such that some or all of those programs and data in the recording medium are downloaded through an electronic network. Additionally, the memory circuitry 73 previously or preliminarily stores 3D model data of a human body diagram in imitation of a human body as an example of medical data. Further, the memory circuitry 73 may previously store volume data of the object P which are acquired in advance.

The communication circuit 74 implements various types of information communication protocols according to aspects of networks. The communication circuit 74 connects the image processing apparatus 20 with the controller 44 of the inspection room console 19 and the remote console 40 according to the various types of information communication protocols. In this connection, e.g., electric connection via an electronic network can be applied. For instance, the processing circuitry 57 may acquire volume data of the object P from, e.g., an image server via a network so as to store the acquired volume data in the memory circuitry 53.

For instance, the speaker 75 and the microphone 76 are used when the operator O of the image processing apparatus 20 in the operators room and the medical engineer M communicate with each other by phone or by video call in real time through the communication circuit 74.

The processing circuitry 77 is a processor configured to perform processing of assisting the medical engineer M in adjusting an imaging region and an imaging direction in cooperation with the processing circuitry 57 of the inspection room console 19 by reading out and executing programs stored in the memory circuitry 73 such that X-ray images desired by the operator O of the device 32 are acquired.

As shown in FIG. 3, the processing circuitry 77 implements a selection receiving function 81, an image determination function 82, an operative provisional image generation function 83, a positioning provisional image generation function 84, and a communication function 85. Those functions 81 to 85 are stored in the memory circuitry 73 in the form of programs.

The positioning provisional image generation function 84 may be implemented by the processing circuitry 57 of the inspection room console 19. In this case, the positioning provisional image generation function 84 may be omitted from the processing circuitry 77. Additionally, when the operator O of the device 32 provides the controller 44 with information for setting the desired region and the desired direction via the remote input circuit 43 of the remote console 40, those functions 81 to 85 of the processing circuitry 77 of the image processing apparatus 20 may be implemented by the controller 44 of the remote console 40, instead of the processing circuitry 77.

Next, one of operations performed by the X-ray diagnostic system 1 and the medical image diagnostic system 10 of the present embodiment will be described as an example. First, brief overview of the operation of the X-ray diagnostic system 1 and the medical image diagnostic system 10 will be described.

Figure 4:
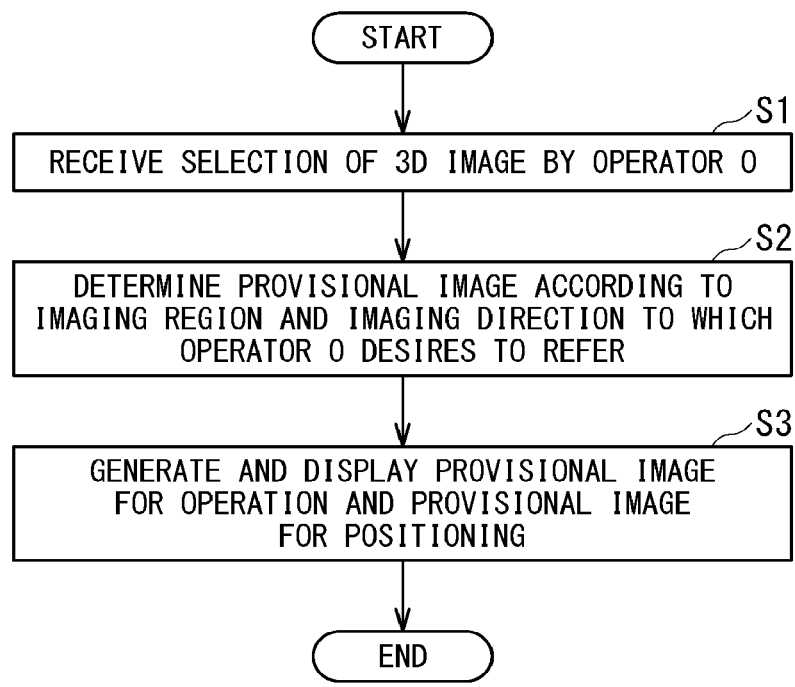
FIG. 4 is a flowchart illustrating processing of assisting a medical engineer in adjusting an imaging region and an imaging direction such that X-ray images desired by an operator of a device are acquired.

FIG. 4 is a flowchart illustrating processing of assisting the medical engineer M in adjusting an imaging region and an imaging direction such that X-ray images desired by the operator O of the device 32 are acquired.

In FIG. 4, each reference sign composed of S and number on its right side indicates step number of the flowchart.

In the step S1, the X-ray diagnostic apparatus 11 receives s selected single 3D data out of plural 3D model data and volume data of the object P from the operator O via the input circuit 72, the remote input circuit 43, or the touch sensor of the input circuit 41 or 42, and then causes the display disposed at a position visible from the operator O to display the selected 3D data. Note that the above plural 3D model data are examples of medical data, and the input circuit 72, the remote input circuit 43, and the touch sensor of the input circuit 41 or 42 are examples of the designation receiving circuit.

In the next step S2, the operator O rotates, magnifies, or reduces the selected 3D data by operating the input circuit 72 or the remote input circuit 43 while confirming the selected 3D data. In this manner, the operator O causes the display disposed at a position visible from the operator O to display a part of the 3D data corresponding to an imaging region and an imaging direction of an X-ray image which the operator O desires to refer to during manipulation. The X-ray diagnostic apparatus 11 determines a partial image corresponding to the desired region and the desired direction of the selected 3D data (i.e., the imaging region and the imaging direction of the X-ray image which the operator O desires to refer to during manipulation) as a provisional image, according to an operation of the operator O with respect to the selected three-dimensional data.

In the step S3, the X-ray diagnostic apparatus 11 generates an operative image based on the provisional image, and causes the display disposed at a position visible from the operator O to display the operative image. Additionally, the X-ray diagnostic apparatus 11 generates a positioning provisional image based on the provisional image, and causes the display disposed at a position visible from the medical engineer M to display the positioning provisional image. Incidentally, the input circuit 72 or the remote input circuit 43 may receive only a designation of size on 3D data. In this case, the operative provisional image generation function 83 generates the operative provisional image 91 in accordance with the designated size, and causes the display 71 to display the generated operative provisional image 91.

Next, details of the operation of the X-ray diagnostic system 1 and the medical image diagnostic system 10 will be described with reference to FIG. 5 to FIG. 9.

Figure 5:
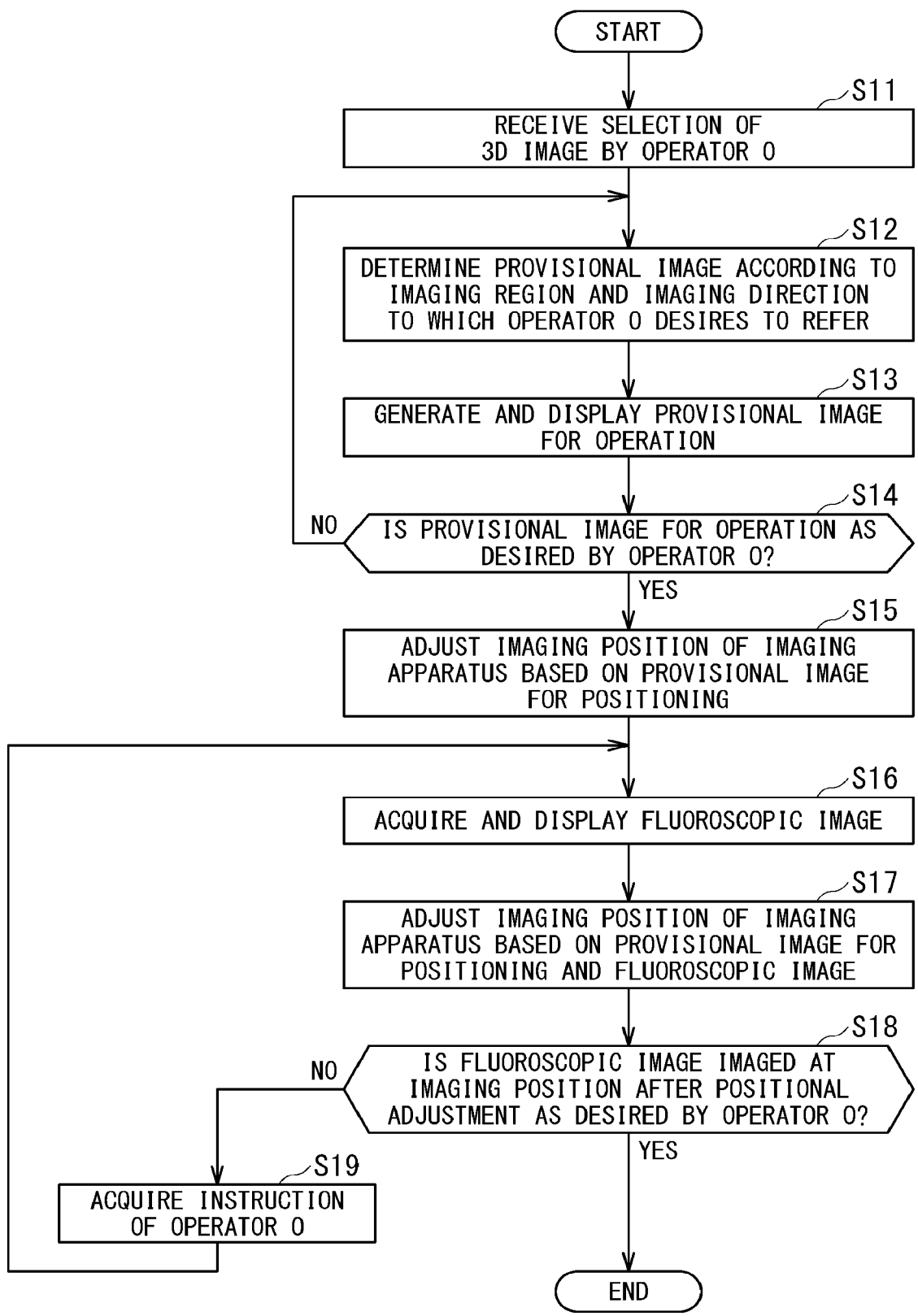
FIG. 5 is a flowchart illustrating details of the flow of processing shown in FIG. 4.
Figure 6:
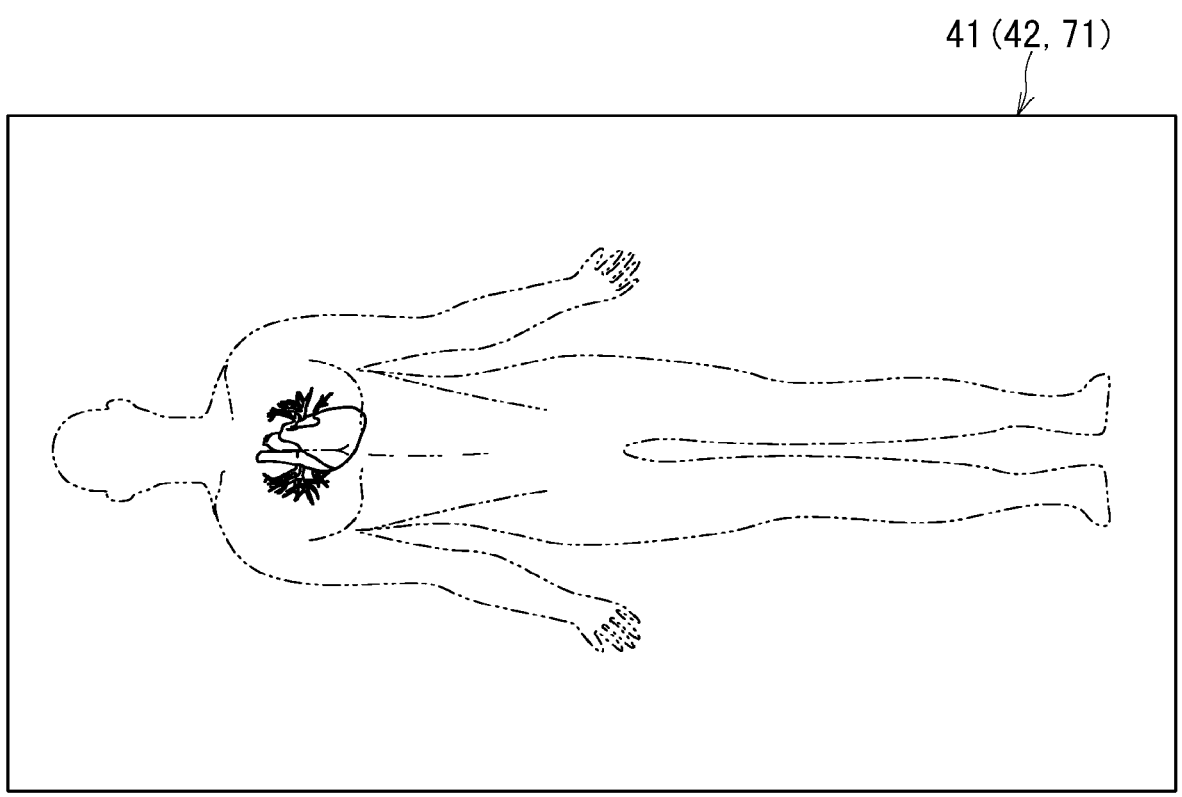
FIG. 6 is a schematic diagram illustrating 3D (three-dimensional) data to be selected.
Figure 7:
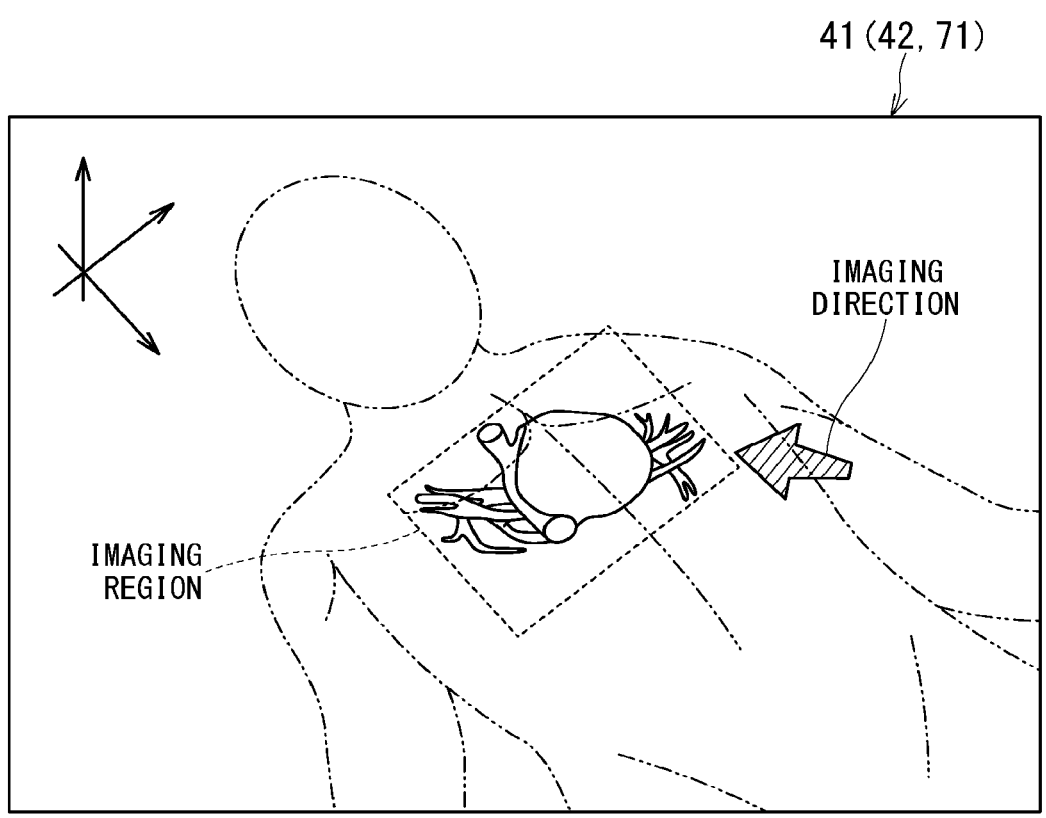
FIG. 7 is a schematic diagram illustrating how a desired region and a desired direction are set to selected 3D data.
Figure 8:
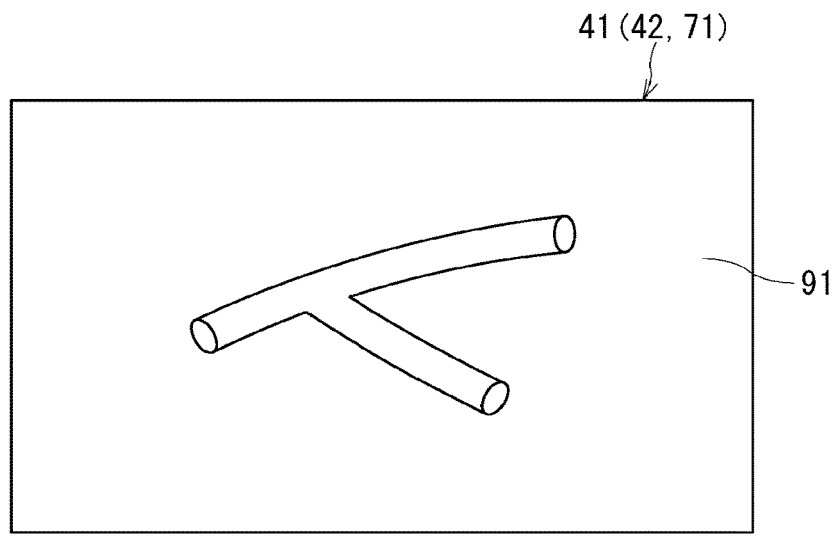
FIG. 8 is a schematic diagram illustrating an operative provisional image generated on the basis of a provisional image.
Figure 9:
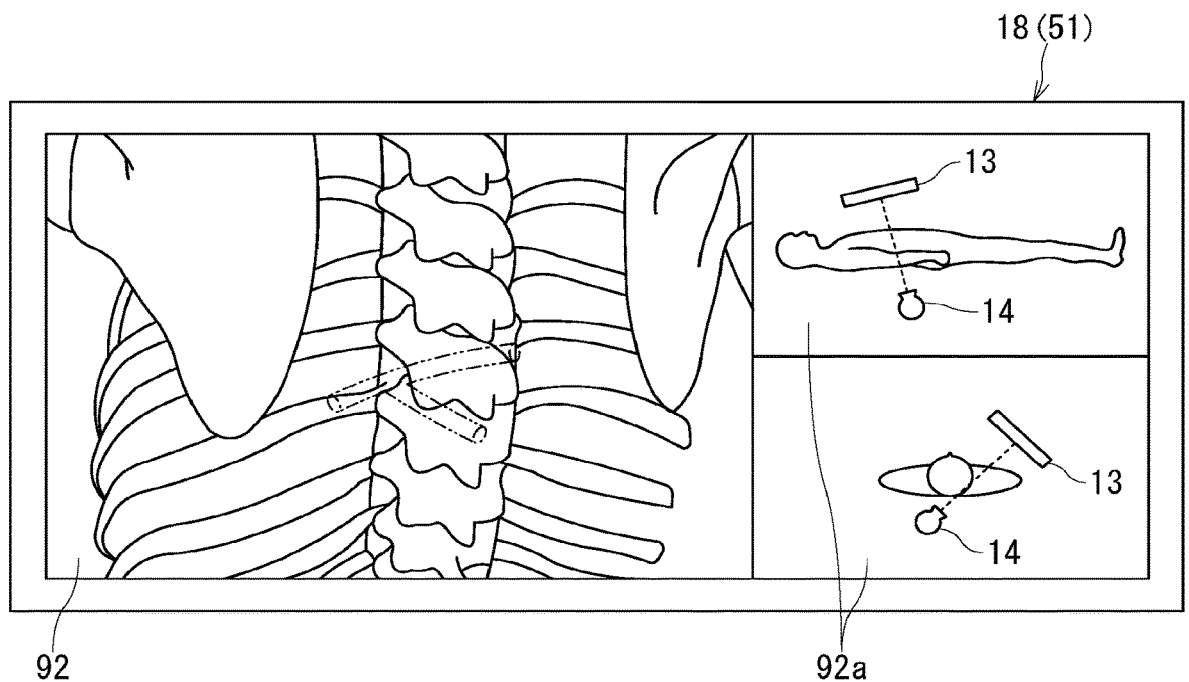
FIG. 9 is a schematic diagram illustrating a positioning provisional image generated on the basis of a provisional image.

FIG. 5 is a flowchart illustrating details of the flow of processing shown in FIG. 4. In FIG. 5, each reference sign composed of S and number on its right side indicates step number of the flowchart. FIG. 6 is a schematic diagram illustrating 3D data to be selected. FIG. 7 is a schematic diagram illustrating how the desired region and the desired direction are set to selected 3D data. FIG. 8 is a schematic diagram illustrating the operative provisional image 91 generated on the basis of the provisional image. FIG. 9 is a schematic diagram illustrating a positioning provisional image 92 generated on the basis of the provisional image.

Incidentally FIG. 5 illustrates a case where the operator O of the device 32 provides the processing circuitry 77 with information for setting the desired region and the desired direction via the input circuit 72 of the image processing apparatus 20 as an example of the designation receiving circuit.

First, in the step S11, the selection receiving function 81 of the image processing apparatus 20 causes the display 71 disposed at a position visible from the operator O to display an image based on the volume data of the object P and respective images indicated by plural 3D model data. Those plural 3D model data are examples of medical data stored in the memory circuitry 73. Note that images to be displayed in the processing shown in FIG. 5 may be displayed on the display(s) of at least one of the display input circuits 41 and 42. Additionally, the selection receiving function 81 receives input for selecting one of the volume data of the object P and plural 3D model data from the operator O via the input circuit 72, and causes the display 71 to display the image indicated by the selected 3D data (FIG. 6).

In the next step S12, while confirming the selected 3D data, the operator O moves, rotates, magnifies, or reduces the selected 3D data by operating the input circuit 72 so as to cause the display 71 to display a part of the selected 3D data corresponding to the imaging region and the imaging direction of the X-ray image which the operator O desires to refer to during manipulation. The image determination function 82 determines the partial image corresponding to the desired region and the desired direction of the selected 3D data (i.e., the imaging region and the imaging direction of the X-ray image which the operator O desires to refer to during manipulation) as the provisional image, according to an operation performed by the operator O with respect to the selected 3D data (FIG. 7).

When the operator O instructs a certain region as the desired imaging region, the image determination function 82 may determine the provisional image by setting the desired region such that at least the instructed region is included in the desired region. Additionally, when the operator O instructs a predetermined position as the desired imaging region, the image determination function 82 may determine the provisional image by setting the desired region such that at least a predetermined range centered on the instructed position is included in the desired region.

In the next step S13, the operative provisional image generation function 83 generates the operative provisional image 91 based on the provisional image so as to cause the display 71 to display the operative provisional image 91. Specifically, as the operative provisional image 91, the operative provisional image generation function 83 generates an image including at least an image, which corresponds to a tubular structure (e.g., a blood vessel) attracting the attention of the operator O during manipulation and is an image observed from the same direction as the desired direction of the provisional image, on the basis of provisional image (FIG. 8). In this case, the operative provisional image 91 may be generated by applying image processing in which blood vessels are emphasized. Preferably, the operative provisional image 91 is such an image that a position of a therapeutic target portion is recognizable or distinguishable for the operator O.

Although it may be preferable that the operative provisional image 91 looks like an image obtained by fluoroscopy or radiography by performing image processing on 3D data (e.g., selected 3D data), an image obtained by performing rendering processing such as volume rendering on 3D data (e.g., selected 3D data) may also be used for the operative provisional image 91. Additionally, the operative provisional image 91 may be a gray-scale image, a color image including chromatic colors, or an image in which only target tubular structures are colored on the basis of a gray-scale image.

In the next step S14, the operative provisional image generation function 83 determines whether the operative provisional image 91 is an image desired by the operator O or not, according to an instruction inputted by the operator O via the input circuit 72. When the operative provisional image 91 is an image desired by the operator O, the provisional image which is the original image of this operative provisional image 91 determined to be an image desired by the operator O is inputted to the positioning provisional image generation function 84 or the determined image acquisition function 61 of the inspection room console 19, and the processing proceeds to the step S15.

Conversely, when the operative provisional image 91 is not satisfactory for the operator O, the processing returns to the step S12 and a series of processing from the steps S12 to S14 is repeated again. In other words, setting of a provisional image (i.e., setting of a desired region and a desired direction) is performed again, then a provisional image is redetermined in the step S12, then the operative provisional image is regenerated in the step S13, and then the processing proceeds to the step S14 again. In this manner, the operator O can use the operative provisional image 91 for determining the provisional image.

Next, in the step S15, the positioning provisional image generation function 84 of the image processing apparatus 20 or the positioning provisional image generation function 62 of the inspection room console 19 generates the positioning provisional image 92 based on the provisional image, and causes the display 18 disposed at a position visible from the medical engineer M to display the generated positioning provisional image 92. In a series of processing shown in FIG. 5, images to be displayed on the display 18 may also be displayed on the display 51.

Specifically, the positioning provisional image generation function 84 or 62 may generate an image satisfying the following first and second conditions as the positioning provisional image 92 based on the provisional image (FIG. 9). The first condition is that the image is viewed from the same direction as the desired direction of the provisional image, and the second condition is to be appropriate for being referred to by the medical engineer M when positioning of at least one of the imaging system and the bed 16 is performed such that X-ray imaging is performed on a region including the desired region in the desired direction.

Although it may be preferable that the positioning provisional image 92 looks like an image obtained by fluoroscopy or radiography by performing image processing on 3D data (e.g., selected 3D data) as well as the operative provisional image 91, an image obtained by performing rendering processing such as volume rendering on 3D data (e.g., selected 3D data) may also be used for the positioning provisional image 92. In other words, the positioning provisional image 92 may be generated by applying image processing which is different from the image processing used for generating the operative provisional image 91.

Additionally, the positioning provisional image 92 may be such an image that distinguishably depicts a part corresponding to the operative provisional image 91. In this case, for instance, a sign or a character string indicative of a part corresponding to the operative provisional image 91 and/or a frame border or a graphic indicative of the range of the operative provisional image 91 may be superimposed on the positioning provisional image 92.

Additionally, the positioning provisional image 92 may be generated in such a manner that the center of the positioning provisional image 92 matches the center of the operative provisional image 91.

Further, it may be preferable that the positioning provisional image 92 is generated so as to include an image of a bone which has a high X-ray absorption coefficient and is easily recognized in a fluoroscopic image. In this case, the positioning provisional image 92 may be generated by applying image processing in which bones are emphasized. As to generation of the positioning provisional image 92, an image part of a tubular structure such as a blood vessel included in the operative provisional image 91 may be superimposed on the positioning provisional image 92 (two-dot chain line in 92 of FIG. 9), and the positioning provisional image 92 may be generated so as not to include a blood vessel. When 3D data being the original image of the provisional image are past volume data of the object P and a portion with a high X-ray absorption coefficient such as a stent is placed inside the object P, the positioning provisional image 92 may be generated so as to include such type of portion. Additionally, it may be preferable that the positioning provisional image 92 is generated as an image of a wider field of view than the operative provisional image 91. This is so that the positioning provisional image 92 can be easily used for adjusting positional relationship between the imaging system and the bed 16.

Moreover, the positioning provisional image generation function 84 or 62 may generate an angle-information image 92a indicative of an angle of the X-ray irradiation axis of the imaging system with respect to the bed 16 on the basis of information on the desired direction of the determined provisional image so as to cause the display 18 to display the angle-information image 92a (FIG. 9). At the timing when the provisional image is determined and the desired direction is determined, the angle of the X-ray irradiation axis of the imaging system with respect to the bed 16 can be determined. Note that since there are various positional relationships between the bed 16 and the object P, it is difficult to determine the X-ray irradiation position. However, by proposing the angle of the X-ray irradiation axis of the imaging system with respect to the bed 16 and the angle-information image 92a indicative of the irradiation direction, it is possible to assist the medical engineer M in performing positioning of at least one of the imaging system and the bed 16 such that X-ray imaging is performed on a region including the desired region in the desired direction. The angle-information image 92a may be an image in imitation of the imaging system and the bed 16 like FIG. 9, texture information indicative of the angle of the X-ray irradiation axis of the imaging system with respect to the bed 16, or combination of both.

The medical engineer M roughly adjusts positional relationship between the imaging system and the bed 16 based on the positioning provisional image 92 and the angle-information image 92a displayed on the display 18 by the positioning provisional image generation function 84 or 62, without irradiating the object P with X-rays.

In the next step S16, according to an instruction of the medical engineer M via the input circuit 52, the fluoroscopic image acquisition function 63 acquires fluoroscopic images generated on the basis of X-ray imaging of the object P performed by the imaging apparatus 12 in real-time.

In the next step S17, the positioning provisional image generation function 84 or 62 causes the display 18 to display the positioning provisional image 92 and the updated fluoroscopic image acquired on a real-time basis in parallel, in such a manner that the medical engineer M can compare the positioning provisional image 92 with the updated fluoroscopic image. The medical engineer M finely adjusts the positional relationship between the imaging system and the bed 16, while comparing the positioning provisional image 92 with the updated fluoroscopic image acquired on a real-time basis.

In the next step S18, the operator O determines whether the current fluoroscopic image is sufficient and desirable for performing manipulation. When it is determined to be sufficient and desirable, the operator O provides the fluoroscopic image acquisition function 63 with information indicative of that via the input circuit 72 so as to stop X-ray irradiation, and thereby a series of processing is completed. As a result, the positional relationship between the imaging system and the bed 16 of the imaging apparatus 12 becomes such relationship that the operator O can acquire desired X-ray images with operational help of the medical engineer M.

Conversely, when the operator O determines that the current fluoroscopic image is not sufficient or desirable, in the step S19, the operator O requests the medical engineer M to readjust the positional relationship between the imaging system and the bed 16 of the imaging apparatus 12, and the medical engineer M acquires detailed instructions for readjusting the positional relationship. The methods of informing the detailed instructions for readjustment via the communication function 85 of the image processing apparatus 20 and communication function 64 of the inspection room console 19 include telephone, videotelephone, transmission/reception of e-mails, and chat and the like. When the instruction from the operator O is received the processing returns to the step S16, and the positional relationship between the imaging system and the bed 16 is readjusted.

In the above-described manner, it is possible to assist the medical engineer M in adjusting the imaging region and the imaging direction such that X-ray images desired by the operator O of the device 32 are acquired.

The X-ray diagnostic apparatus 11 of the present embodiment can present the operator O with the operative provisional image 91 appropriate for manipulation based on the desired region and the desired direction determined by the operator (FIG. 8), and can present the medical engineer M with the positioning provisional image 92 appropriate for adjusting the positional relationship between the imaging system and the bed 16 (FIG. 9). Thus, according to the X-ray diagnostic apparatus 11, the medical engineer M in the inspection room can easily and accurately adjust the positional relationship between the imaging system and the bed 16 such that images deserted by the operator O of the device 32 are acquired.

Additionally, the X-ray diagnostic apparatus 11 can generate the angle-information image 92a indicating the angle of the X-ray irradiation axis of the imaging system with respect to the bed 16 based on the desired direction determined by the operator O so as to cause the display 18 to display the angle-information image 92a (FIG. 9). Thus, the medical engineer M can adjust the positional relationship between the imaging system and the bed 16 more quickly.

Further, according to a series of processing shown in FIG. 5, after roughly adjusting the positional relationship between the imaging system and the bed 16 without irradiating the object P with X-rays, the positional relationship can be finely adjusted by using fluoroscopic images. Thus, X-ray exposure of the object P during adjustment of the positional relationship can be drastically reduced.

Incidentally, the communication circuit 54 of the present embodiment is an example of the communication circuit recited in the claim.

The processing circuitry 57, 77 and processing circuitry of the controller 44 of the remote console 40 in the present embodiment are examples of processing circuitry recited in the claims.

The input circuit 72, the respective touch sensors of the display input circuit 41 and 42, and the remote input circuit 43 in the present embodiment are examples of the designation receiving circuit recited in the claims.

The respective touch sensors of the display input circuits 41 and 42 and the remote input circuit 43 in the present embodiment are examples of the operation circuit recited in the claim.

The respective displays of the display input circuits 41 and 42 of the remote console 40 and the display 71 of the image processing apparatus 20 in the present embodiment are examples of the first display recited in the claims.

The display 18 of the inspection room in the present embodiment is an example of the second display recited in the claims.

The term "processor" used in the processing circuitry 57, 77 of the image processing apparatus 20 and the processing circuitry of the controller 44 of the remote console 40 in the above-described embodiments, for instance, refer to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although FIG. 2 and FIG. 3 show an example in which the processing circuitry configured of a single processor implements respective functions, the processing circuitry may be configured by combining plural processors independent of each other such that each processor implements each function of the processing circuitry by executing corresponding program. When plural processors are provided for the processing circuitry, memory circuitry for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For instance, an X-ray CT (Computed Tomography) apparatus capable of CTF (Computed Tomography Fluoroscopy) may be used instead of the X-ray diagnostic apparatus 11 of the present embodiment.

Moreover, in the embodiments of the present invention, although an example of processing in which each step of a flowchart is executed along a time series according to the described order has been shown, the processing may not necessarily be performed along the time series, and may be performed in parallel or individually.

The invention claimed is:

1. An X-ray diagnostic method using an X-ray diagnostic system and an operation apparatus for operating, from a position separated from an object, a device inserted inside the object, the X-ray diagnostic comprising:
   an imaging apparatus including an X-ray source and an X-ray detector and configured to perform X-ray imaging to generate an X-ray image of the object;
   a first display disposed at a position visible from a first user who operates the device; and
   a second display disposed at a position visible from a second user who performs positioning of the imaging apparatus, the position of the second display being separated from the position of the first display;
   the method comprising:
      acquiring 3D image data including three-dimensional medical image data of the object or three-dimensional model data imitating a human body,
      generating, from the 3D image data, a provisional image that is a partial image of the 3D image data, wherein the partial image corresponds to a desired region and a desired direction to be set by the first user who operates the device,
      generating a first image configured to be observed from a same direction as the desired direction based on the provisional image, wherein the first image includes at least a blood vessel and is generated by applying image processing in which the blood vessel is emphasized,
      using the first display to display the first image such that the first user is able to evaluate the first image, and
      generating a second image configured to be observed from a same direction as the desired direction based on the provisional image, wherein the second image is different from the first image, includes at least a bone, and is generated by applying image processing in Which the bone is emphasized, and
      using the second display to display the second image such that the second user is able to adjust a positional relationship between the imaging apparatus and a bed on which the object is placed, while comparing the second image with the X-ray image of the object acquired on a real-time basis.

2. The X-ray diagnostic method according to claim 1, wherein the first display and a designation receiving circuit are provided on a same console.

3. The X-ray diagnostic method according to claim 2, wherein the designation receiving circuit is configured to further receive a designation of an imaging direction on the 3D image data.

4. The X-ray diagnostic method according to claim 3, comprising displaying a chart indicating the designated imaging direction on the second display.

5. The X-ray diagnostic method according to claim 2, wherein
   the designation receiving circuit is configured to receive a designation of size on the 3D image data; and
   the method comprises displaying the first image according to the designated size on the 3D image data on the first display.

6. The X-ray diagnostic method according to claim 1, comprising generating the second image to be viewed from a same direction as the first image.

7. The X-ray diagnostic method according to claim 6, wherein a center of the second image matches a center of the first image.

8. The X-ray diagnostic method according to claim 6, wherein the second image is wider in field of view than the first image.

9. The X-ray diagnostic method according to claim 8, wherein the second image distinguishably depicts a part corresponding to the first image.

10. The X-ray diagnostic method according to claim 6, wherein
    the 3D image data are volume data, and
    the method comprises generating the first image and the second image from the volume data.

11. The X-ray diagnostic method according to claim 1, wherein:
the 3D image data are medical image data; and
the second image is generated by applying image processing which is different from image processing applied to generation of the first image.

12. The X-ray diagnostic method according to claim 11, comprising superimposing a portion of the first image on the second image.

13. The X-ray diagnostic method according to claim 11, wherein the second image is generated by applying image processing for emphasizing each bone.

14. The X-ray diagnostic method according to claim 11, wherein the first image is generated using volume rendering.

15. The X-ray diagnostic method according to claim 14, wherein the second image is generated in such a manner that any blood vessel is not depicted in the second image.

16. The X-ray diagnostic method according to claim 11, wherein the first image is generated by applying image processing for emphasizing each blood vessel.

17. An X-ray diagnostic method using an X-ray diagnostic system and an operation apparatus for operating, front a position separated from an object, a device inserted inside the object, the X-ray diagnostic system comprising:
an imaging apparatus including an X-ray source and an X-ray detector and configured to perform X-ray imaging to generate an X-ray image of the object;
a first display outside an inspection room where the imaging apparatus is disposed and disposed at a position visible from a first user who operates the device; and
a second display inside the inspection room and disposed at a position visible from a second user Who performs positioning of the imaging apparatus;
the method comprising:
acquiring 3D image data including three-dimensional medical image data of the object or three-dimensional model data imitating a human body,
generating, from the 3D image data, a provisional image that is a partial image of the 3D image data, wherein the partial image corresponds to a desired region and a desired direction set by the first user who operates the device,
generating a first image configured to be observed from a same direction as the desired direction based on the provisional image, wherein the first image includes at least a blood vessel and is generated by applying image processing in which the blood vessel is emphasized,
using the first display to display the first image such that the first user is able to evaluate the first image, and
generating a second image configured to be observed from a sane direction as the desired direction based on the provisional image, wherein the second image is different from the first image, includes at least a bone, and is generated by applying image processing in which the bone is emphasized, and
using the second display to display the second image such that the second user is able to adjust a positional relationship between the imaging apparatus and a bed on which the object is placed, while comparing the second image with the X-ray image of the object acquired on a real-time basis.

18. The X-ray diagnostic method according to claim 17, wherein the first display and a designation receiving circuit are provided on a same console.

19. The X-ray diagnostic method according to claim 18, wherein the designation receiving circuit is configured to receive a designation of size on the 3D image data; and
the method comprises displaying the first image according to the designation of size on the 3D image data on the first display.

20. The X-ray diagnostic method according to claim 18, further comprising a communication circuit configured to realize communication of a voice information between inside of the inspection room where the designation receiving circuit and the first display are disposed and outside of the inspection room.

21. The X-ray diagnostic method according to claim 17, comprising generating the second image to be viewed from a same direction as the first image.

22. The X-ray diagnostic method according to claim 17, wherein:
the 3D image data are medical image data; and
the second image is generated by applying image processing which is different from image processing applied to generation of the first image.

23. A medical image diagnostic method using a medical diagnostic system that includes a device for medical treatment on an object and arm X-ray fluoroscopic apparatus that includes an X-ray source and an X-ray detector and is configured to perform X-ray imaging of the object, and is configured to remotely control the device from a position separated from the object during the medical treatment on the object with fluoroscopic imaging of the object performed by the X-ray fluoroscopic apparatus, the medical image diagnostic comprising:
a console including a first display disposed at a position visible from a first user who operates the device; and
a second display disposed at a position which is separated from the console and visible from a second user who performs positioning of the X-ray fluoroscopic apparatus;
the method comprising:
acquiring 3D image data including three-dimensional medical image data of the object or three-dimensional model data imitating a human body,
generating, from the 3D image data, a provisional image that is a partial image of the 3D image data, wherein the partial image corresponds to a desired region and a desired direction to be set by the first user who operates the device,
generating a first image configured to be observed from a same direction as the desired direction based on the provisional image, wherein the first image includes at least a blood vessel and is generated by applying image processing in which the blood vessel is emphasized,
using the first display to display the first image such that the first user is able to evaluate the first image,
generating a second image configured to be observed from a same direction as the desired direction based on the provisional image, Wherein the second image is different from the first image, includes at least a bone, and is generated by applying image processing in which the bone is emphasized, and configuring the second image to be displayed on the second display such that the second user adjusts is able to adjust a positional relationship between the imaging apparatus and a bed on which the object is placed, while comparing the second image with an X-ray image of the object acquired on a real-time basis.

* * * * *